US006833060B2

(12) United States Patent
Harding et al.

(10) Patent No.: US 6,833,060 B2
(45) Date of Patent: Dec. 21, 2004

(54) ELECTROPHORESIS GEL SUPPORT

(75) Inventors: George Harding, Louisville, KY (US); Elias Klein, Louisville, KY (US); Jon Klein, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 93 days.

(21) Appl. No.: 09/850,540

(22) Filed: May 7, 2001

(65) Prior Publication Data

US 2002/0027076 A1 Mar. 7, 2002

Related U.S. Application Data

(60) Provisional application No. 60/202,264, filed on May 5, 2000.

(51) Int. Cl.[7] ..................... G01N 27/453; G01N 27/447
(52) U.S. Cl. ....................... 204/466; 204/456; 204/464; 204/616; 204/606; 204/614
(58) Field of Search ................................ 204/455, 456, 204/464, 465, 466, 605, 601, 451, 606, 614, 615, 616

(56) References Cited

U.S. PATENT DOCUMENTS

| | | | |
|---|---|---|---|
| 3,939,237 A | | 2/1976 | Naito et al. .................... 264/54 |
| 4,680,201 A | | 7/1987 | Hjerten ........................ 427/230 |
| 4,740,104 A | | 4/1988 | Stohr et al. ................... 405/36 |
| 4,891,119 A | * | 1/1990 | Ogawa ........................ 204/469 |
| 5,114,555 A | * | 5/1992 | Stimpson .................... 204/601 |
| 5,447,617 A | | 9/1995 | Shieh ..................... 204/299 R |
| 5,637,202 A | * | 6/1997 | Harrington et al. ......... 204/469 |
| 5,637,224 A | | 6/1997 | Sirkar et al. ................. 210/644 |
| 5,837,116 A | | 11/1998 | Harrington et al. ......... 204/606 |
| 5,858,188 A | | 1/1999 | Soane et al. ................. 204/454 |

FOREIGN PATENT DOCUMENTS

| | | | |
|---|---|---|---|
| DE | 20017414 | 12/2001 | ............ C07K/1/26 |
| EP | 0477541 A2 * | 4/1992 | ......... G01N/27/447 |
| JP | 03002556 A * | 1/1991 | ......... G01N/27/447 |

OTHER PUBLICATIONS

English language translation of Hei 3–2556 (Tsutomu Nishine).*
Information on Glass Containers, downloaded from www.gpi.org/Info_on. html, Dec. 18, 2003.*
JPO abstract of JP 03–002556–A (Nishine).*
Caplus abstract of Wolfram et al. ("Wetting of polymers in aqueous solutions of alkyl sulfate," Kolorisztikai Ertesito (1970), 12(1–2), 2–7).*
Anderson, N., et al., "Twenty Years of Two–Dimensional Electrophoresis: Past, Present and Future", *Large Scale Biology Corporation*, http://www.1sbc.com/papers/draf0046.htm, Draft of Paper published in Electrophoresis, 17, 443–453, 1994, pp. 1–13, (1994).

* cited by examiner

*Primary Examiner*—Alex Noguerola
(74) *Attorney, Agent, or Firm*—Fish & Richardson P.C., P.A.

(57) ABSTRACT

The present invention relates generally to the electrophoretic separation of biomolecules, including but not limited to proteins, peptides, DNA and RNA. The methods of this invention are particularly useful when applied to two-dimensional gel electrophoresis.

12 Claims, 4 Drawing Sheets

ELECTROPHORESIS GEL SUPPORT

CROSS-REFERENCE TO RELATED APPLICATIONS

This application claims priority based on U.S. Provisional Patent Application Ser. No. 60/202,264, filed May 5, 2000, which is hereby incorporated by reference in its entirety.

FIELD OF THE INVENTION

The present invention relates generally to the electrophoretic separation of biomolecules, including but not limited to, proteins, peptides, DNA and RNA.

BACKGROUND OF THE INVENTION

Two-dimensional gel electrophoresis is well known. Using this technique, a complex mixture of biological material can be resolved into its components based on two independent variables, such as charge and mass. A first gel separation, based on the isoelectric point of biomolecules as one method of separation, is generally run in a tube. The biological sample is placed at the top of a tube containing a gel and an electric current is applied. After electrophoretic separation of the biomolecules, the gel is then removed from the tube and placed across the top of a slab gel and the second method of separation is performed. The resulting two-dimensional array will display discrete spots that are not separable with any single electrophoretic separation.

Many methods of electrophoretic separation or sample treatment are known and have been used in various combinations for two-dimensional gel electrophoresis. These include polyacrylamide gel electrophoresis (PAGE: separation by charge-mass migration in an electric field), SDS-PAGE (separation by mass of sample treated with detergent), isoelectric focusing (IEF: separation by isoelectric point in a pH gradient), and enzymatic digestion after the first separation and before the second separation. All of these methods are well known to those skilled in the art of analysis of biological materials and the choice such an artisan will make is dependent on the nature of the material and the information sought to be elucidated.

For purposes of electrophoresis, it is necessary to form the gel by polymerization of monomers in a support. The properties of the gel can be varied as desired by varying the monomer content and the degree of cross-linking. The resulting gels are fragile, particularly those of low polymer content, such as five percent (5%), which are useful for separating molecules of high molecular weight. The most commonly used support has been glass. However, glass has a strong surface negative charge causing electroosmotic flow, which distorts the separation. Removal of the gel from the first run can be difficult because of the attraction of the gel to the glass. In addition, high frictional coefficients add to the problem of removal, particularly when very small-bore tubing, that is, capillaries, are used.

U.S. Pat. No. 5,447,617 describes covalently bonding polybutadiene to the inner surface of a capillary tube in an attempt to eliminate these problems. U.S. Pat. No. 4,680,201 reaches the same result by bonding a monomer layer to the inner surface of some glass tubes and polymerizing the monomer in situ. U.S. Pat. No. 5,858,188 discloses microchannels in the form of a variety of configurations, including capillaries, having an inner surface coated with acrylic polymer.

The need remains to provide an improved gel support for electrophoresis.

SUMMARY OF THE INVENTION

This invention comprises an improved gel support tube formed of a selectively permeable microporous polymer for use in electrophoresis. The microporous tube is selected to be non-wettable during the first procedure, preventing the sample from escaping through the micropores. Such microporous tubes have been made, by way of example and without limitation, from polyethylene, polypropylene, polystyrene, polycarbonate, polysulfone and the like. The sizes of the pores are easily varied. The pore size chosen is dependent on the substances to be separated, with larger pores being more useful for large molecules. The only limitation on material and pore size is that the material must be nonwettable in the absence of detergent or organic solvent and wettable in the presence of detergent or organic solvent. The pore size must be large enough so as not to impede the passage of large molecules nor so small that biological samples leak through during the first separation. Following electrophoretic separation of biological materials the separated components can be removed through the pores of the support by treatment with detergent, which renders the pores permeable to the sample, followed by electrophoresis or absorption onto a surface.

The size of the support tube can be varied according to whether the separation is preparative or for the purposes of identification of the separated biological material. Frequently, it is desired to use small samples of material. In that case, the support tube selected will be small and, for purposes of describing this invention, is termed a "fiber."

This invention further comprises a method of performing two-dimensional gel electrophoresis which eliminates the step of removal of the gel from the tube of the first dimensional run before placing the gel in the second dimensional apparatus. The entire tube is placed on the second dimension gel. During the second run, the electrophoretic solution contains a wetting agent, so that the components of the sample may be driven through the pores by the electric field into the second dimension slab gel. The second dimension can be run directly with the gel of the first dimension, or after the gel of the first dimension is subjected to further treatment. A common further treatment is the digestion of the biological material by a degradative enzyme. When the sample is a protein, it is often desirable to break the protein into fragments with a proteinase such as trypsin or papain.

This invention also comprises a means to form an acrylamide gel within a protective sheath so as to prevent ambient oxygen from interfering with polymerization. The support tube is inserted into a polymer sheath, as long as or longer than the support tube and of a diameter just sufficient to allow insertion of the support tube into the protective sheath.

This invention also comprises a means of eluting separated components of a biological sample onto nylon mesh or filter paper.

DETAILED DESCRIPTION OF THE INVENTION

The following embodiments are intended to illustrate the use of the present invention and are not intended to limit its scope in any way.

EXAMPLE 1

Selection of Non-wettable Microporous Polymer Tubing

Polyethylene tubing (Asahi Chemical Co., Tokyo, Japan) of 0.7 to 1.5 mm inside diameter or polypropylene of similar dimensions (Membrana Gmbh, Wuppertal, Germany), having porosities in the range of 40–75% void fraction with average pore dimensions of 0.05 to 1.0 $\mu$m, preferably 0.1 to 0.7 $\mu$m, is used for the preparation of the IEF gels for this embodiment. It may be desirable to wash vessels and spinning aids by washing with strong base, water and a polar, volatile solvent in order to remove contaminants that might interfere with the polymerization of the acrylamide gels. Some porous tubing may not need such a cleansing. Because the walls of the tubing are highly permeable to oxygen in the air which interferes with acrylamide polymerization, the porous tubes are covered before use with an impermeable protective tube, as long or longer than the tubes and slightly greater in diameter, so as to allow insertion of the support tube, but provide a snag fit. An inert gas is then forced through the wall of the tube by perfusing the lumen and forcing the gas to escape through the annulus between the porous tube and the protective sheath. The tubing can be fixed to the fiber mechanically in a number of ways to maintain the integrity of the sheath layer. Once the dry porous tubing has been freed of oxygen, the assembly is ready for introduction of the gel forming solution consisting typically of acrylamide and a cross-linking agent, such as bis-acrylamide and selected other components.

EXAMPLE 2

Isoelectric Focusing

Generally, buffer that has been deaerated is used to dissolve the selected amount of acrylamide monomer powder. The selected amount can vary from two to thirty percent (2–30%) w/v. The cross-linking agent is commonly bis-acrylamide in concentrations from 0.2 to 2% w/v. One skilled in the art will select a gel with low (4–6%) acrylamide content and low cross-linking for very large molecules such as proteins. Such a gel is extremely soft and difficult to handle.

IEF was chosen for the first separation of a test protein mixture (Biorad #161-0390 Biorad, Inc. Redmond, Calif.). The gel was prepared from a stock solution of 30% acrylamide and 0.4%–1.8% bis-acrylamide. This solution was diluted 1:4.5 to 1.7 in a graduated cylinder containing enough urea crystals to produce a gel that is 8.0M in urea and 2% ampholytes (Genomic Solutions, Inc., Ann Arbor, Mich.) of the desired pH range (3–10) and 1 $\mu$l of TEMED/ml of monomer solution was added. To this solution was added the catalyst mixture containing 5–10 $\mu$l/ml of 10% $Na_2S_2O_8$.

Figure 1:
FIG. 1 shows extruded gels from an IEF separation, stained with Coomassie Blue.

Various lengths of the plastic tubing (here termed "fiber" to differentiate it from the support tubing) were fitted into sheaths of dense polyethylene tubing with an internal diameter that fit snugly around the fiber. The dense sheath had a vent port punched near the top end of the sheath, to allow the inert gas to cross the fiber wall and vent to the atmosphere. The inert gas chosen was nitrogen, but helium or argon are also easily available and useable in this invention. The junction between the sheath and fiber was closed with a suitable non-permeable material at both ends of the module. These constructed modules were placed on a gas manifold in the vertical orientation with the vent port at the top, the lumen of the fiber was plugged and the inert gas perfused across the lumen wall. Catalyzed monomer solution was quickly filled into the lower lumen opening of the fiber via a three-way stopcock used for inert gas perfusion until the monomer solution filled the entire length of the tubing lumen. The polymerization was allowed to proceed for several hours and the final tubing was then cut into convenient lengths. Generally the length was chosen to be that of the width of the slab for the second separation, that is, 15 cm. The vented end of each fiber segment was fitted with a suitable sample reservoir adapter to allow attachment to the IEF apparatus and introduction of the sample mixture. A protein protection solution consisting of 4.5M urea, 0.2% Triton X 100, 0.1% ampholytes, 0.05M dithiothreitol (DTT) was introduced into the sample reservoir and the gel was then prefocused for one hour. At the end of the prefocusing period, the sample (9 $\mu$l of the Biorad IEF protein standard, 16.5 mg/250 $\mu$l) was introduced below the protective solution. The assembly is subjected to a further 11 hours of electrofocusing using incremental increases in applied voltage, selected so that excessive resistance heating did not occur. As a result of the applied electric field, the ampholytes and the test proteins moved to their pH equilibrium positions, as shown in FIG. 1. On the left ("Naked gel") is a two-dimensional gel from a standard IEF gel in which the gel is pushed out from the support. On the right ("Fiber") is a second dimension gel run using the microporous hollow fiber technique of this invention. Both gels were loaded with equal amounts of the protein standards. Comparison of the extruded gels, in which the proteins were stained with Coomassie Blue shows the reproducibility of the electrophoretic separation. It is readily apparent that the protein sample migrated through the hollow fiber into the second dimension. The protein spot resolution is excellent in the fiber gel and may actually be better than in the naked gel

EXAMPLE 3

Second Dimension Sodium Dodecyl Sulfate Polyacrylamide Gel Electrophoresis (SDS-PAGE)

A second dimension SDS-PAGE gel was cast from the same monomer and cross-linker stock solution, diluted 1:3 with tris buffer and water containing 0.1% SDA in addition to the catalyst solution. A 15×15×0.1 cm gel was prepared by filling the space between two glass plates and allowing the solution to polymerize. The electrofocused gel from example 2 was then conditioned in a 0.1% SDS solution containing bromphenol blue, 0.5 mg DTT/ml (dithiothreitol) and sufficient propanol to permit wetting of the fiber pore structure. To reduce dimensional changes of the gel the end of the porous fiber was sealed.

Figure 2:
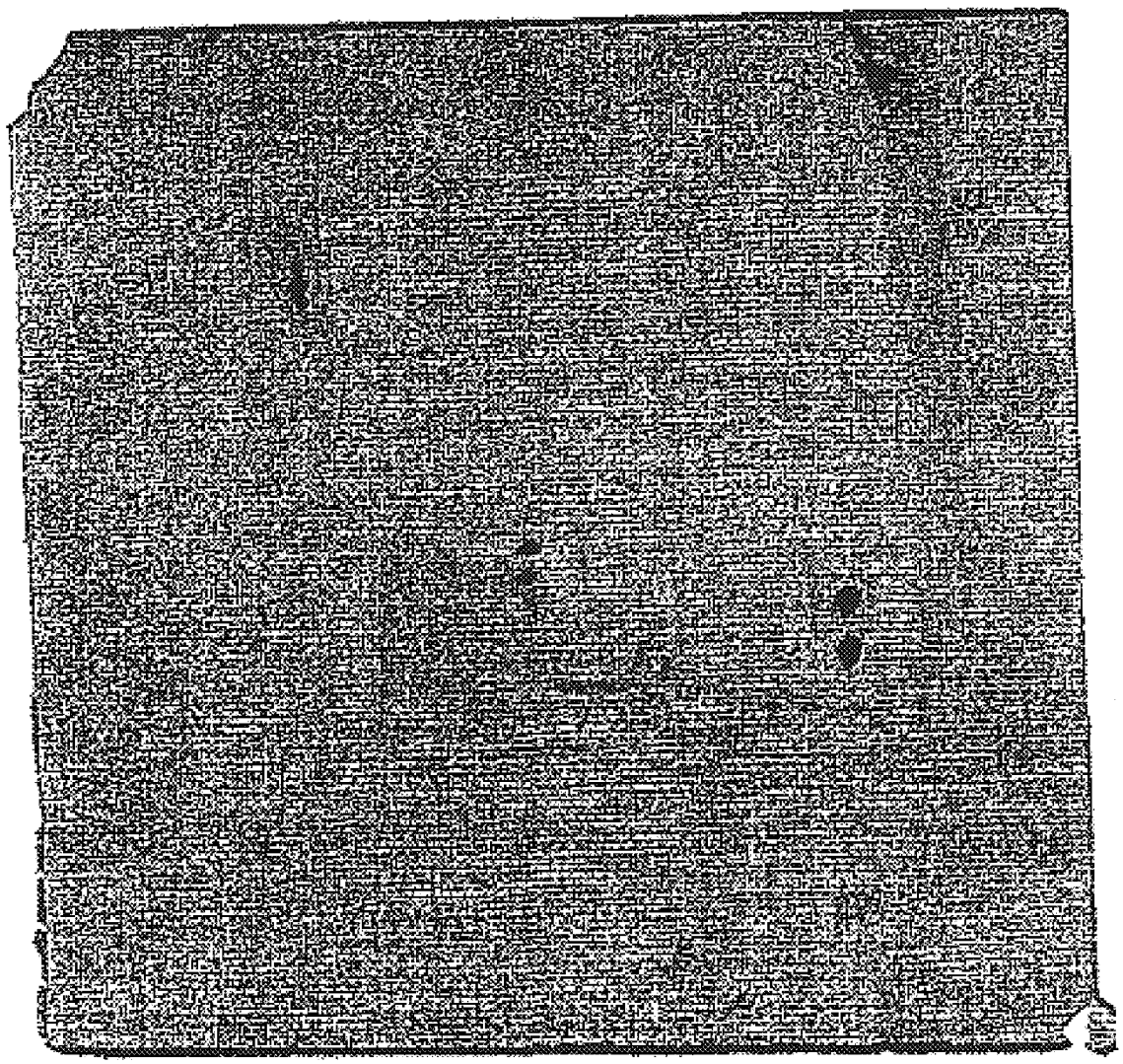
FIG. 2 shows a second dimension slab gel, stained with silver.

Meanwhile, a solution containing 0.2 g SDS in 174 ml water, 25 ml of trisphosphate buffer pH 7.4 made 1.5% in agarose was placed on top of the SDS-PAGE gel to receive the electrophoresed fiber from the first separation. Once the fiber was in place on top of the gelled agarose the fiber was over-layered with molten agarose solution to provide electrical continuity and positional stability of the fiber with the SDS-PAGE reservoirs bathing the upper and lower edges of the slab gel. A typical second dimensional gel of a four component protein mixture stained with silver is shown in FIG. 2.

EXAMPLE 4

Other First Separation Methods

Figure 3:
FIG. 3 shows extruded gels from an IEF separation in a highly cross-linked gel, stained with Coomassie Blue.

A mixture of 30% acrylamide and 0.6% bis-acrylamide were polymerized as in Example 2, to produce a more highly cross-linked gel containing the urea denaturant and the mobile ampholytes. A protein mixture was electrophoresed as described previously and the gel containing the separated proteins was extruded from the porous housing to examine the quality of the separation. Despite the preferred higher level of cross-linking, the proteins were found to be well-separated into tight bands, as illustrated in FIG. 3. The use of the higher level of cross-linking is sometimes desired to minimize the extent of gel swelling during conditioning with the SDS surfactant and electrophoresis in the second dimension, due to the high molarity of urea in the gel.

EXAMPLE 5

Elution of Separated Components and Digestion into Fragments

After either the first or the second separation, the proteins from the gel can be transferred to a support medium for further analysis. FIG. 3 shows a second dimension SDS-PAGE gel stained with Coomassie Blue. Selected stained proteins from the gel were subjected to trypsin proteolysis and the resulting peptides were analyzed by MALDI Mass Spectrometry. The trypsin digestion can be performed on either small pieces excised from the gels or on the entire gel by electroblotting the protein through a layer of immobilized trypsin onto a receiving hydrophobic membrane, as described by Biervenut et al. (Biervenut, et al. "Toward a Clinical Molecular Scanner for Proteome Research: Parallel Protein Chemical Processing before and during Western Blot" Anal. Chem. (1999) 71: 4800–4808).

Alternatively, the fiber containing the first separation can be placed on top of the slab gel, trypsin solution added to the reservoir, and electric current applied sufficiently long enough to drive the trypsin into the fiber. The current is then discontinued and digestion allowed to take place. The current is then reapplied and separation of the peptides allowed to take place.

EXAMPLE 6

Separation of a Complex Mixture of Proteins

Figure 4:
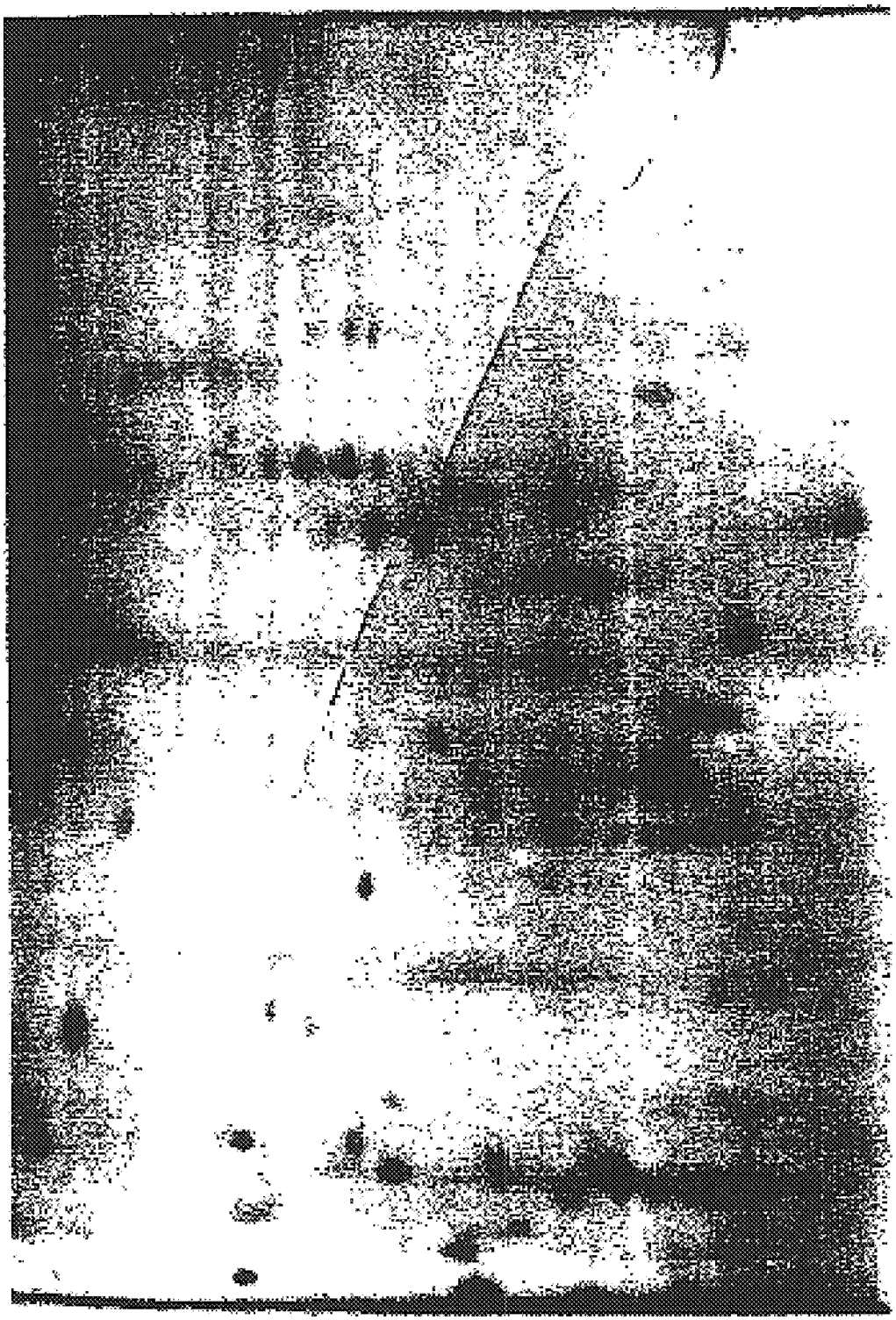
FIG. 4 shows the separation of a complex mixture of proteins on a two dimensional gel.

FIG. 4 shows the power of resolution of this invention for a complex mixture of protein. The total protein extract from mouse fibroblasts was prepared by standard methods and separated in two dimensions by the method of Example 2. The sensitivity and spot resolution are excellent, showing that the methods of this invention can be used with complex mixtures, containing more than twenty proteins, which are able to pass through the pores of the hollow fiber, without adversely affecting resolution.

The invention has been described in terms of certain embodiments. One skilled in the art can, without undue experimentation, make variations or modifications in the compositions or methods described herein without departing from the concept and scope of the invention. All such variations or modifications are considered to be within the scope of the appended claims. In addition, the methods and structure of the present invention can be incorporated in the form of a variety of embodiments, only a few of which are described herein. It will be apparent to the artisan that other embodiments exist that do not depart from the spirit of the invention. Thus, the described embodiments are illustrative and should not be construed as restrictive.

All patents and references cited herein are, insofar as they may be useful to describe the invention, hereby incorporated by reference.

We claim:

1. A gel electrophoresis support comprising an electrophoresed biological sample within the support and a selectively permeable polymer that is porous and non-wettable in an absence of a detergent or an organic solvent, wherein the polymer has been wetted with a detergent or an organic solvent applied to the polymer that renders the pores of the polymer permeable to the electrophoresed biological sample.

2. The gel electrophoresis support of claim 1, wherein the support comprises a gel that is formed by:
   temporarily inserting the support into a protective sheath having a length equal to or greater than a length of the support and having a diameter slightly greater than a diameter of the support and sufficient to allow insertion of the support;
   filling the support with a monomer solution;
   allowing the monomer solution to polymerize and form the gel; and
   removing the filled support from the protective sheath.

3. The support of claim 1, wherein the polymer comprises polyethylene, polypropylene, polystyrene, polycarbonate, or polysulfone.

4. The support of claim 1, wherein the polymer has a porosity of 40–75% void fraction.

5. The support of claim 1, wherein the support has average pore dimensions of 0.05 to 1.0 µm.

6. The support of claim 1, wherein the detergent comprises sodium dodecyl sulfate.

7. The support of claim 1, wherein the support comprises a tube having two ends.

8. A method to transfer components of a biological sample to a support medium, the method comprising:
   providing a gel electrophoresis support comprising a selectively permeable material that is porous and non-wettable in an absence of a detergent or an organic solvent, wherein the support contains a gel;
   applying the biological sample to one end of the support;
   applying a first electric current sufficient to cause components of the biological sample to migrate in the gel to form an electrophoresed sample;
   wetting the selectively permeable material of the support with the detergent or the organic solvent;
   contacting the support with the support medium; and
   applying a second electric current sufficient to cause the electrophoresed sample to migrate through the selectively permeable material onto the support medium.

9. The method of claim 8, further comprising:
   temporarily inserting the support into a protective sheath having a length equal to or greater than a length of the support and having a diameter slightly greater than a diameter of the support and sufficient to allow insertion of the support;
   filling the support with a monomer solution;
   allowing the monomer solution to polymerize and form the gel; and
   removing the filled support from the protective sheath.

10. The method of claim 8, wherein the support comprises a tube having two ends.

11. The method of claim 8, wherein the detergent comprises sodium dodecyl sulfate.

12. The method of claim 8, wherein the support medium comprises a slab gel.

* * * * *